United States Patent [19]
Greep

[11] Patent Number: 6,066,137
[45] Date of Patent: May 23, 2000

[54] ELECTRIC FIELD CONCENTRATED ELECTROSURGICAL ELECTRODE

[75] Inventor: Darcy W. Greep, South Jordan, Utah

[73] Assignee: MegaDyne Medical Products, Inc., Draper, Utah

[21] Appl. No.: 08/984,716

[22] Filed: Dec. 3, 1997

Related U.S. Application Data

[63] Continuation-in-part of application No. 08/943,551, Oct. 3, 1997.

[51] Int. Cl.$^7$ ...................................................... A61B 18/14
[52] U.S. Cl. .................................. 606/45; 606/49; 606/51
[58] Field of Search .................................. 606/41, 45, 48, 606/49, 50–52

[56] References Cited

U.S. PATENT DOCUMENTS

| | | |
|---|---|---|
| 4,534,347 | 8/1985 | Taylor . |
| 4,674,498 | 6/1987 | Stasz . |
| 4,785,807 | 11/1988 | Blanch . |

*Primary Examiner*—Lee Cohen
*Attorney, Agent, or Firm*—Workman, Nydegger & Seeley

[57] ABSTRACT

An electric field concentrated electrosurgical electrode (e.g., blade, forceps or the like) wherein there is provided a conducting member having an edge that is at least partly sharpened and coated over most of its surface with electrical insulating non-stick material so as to produce a an instrument having a slightly projecting uncoated region to produce a highly concentrated electric field and a highly concentrated transfer of electric energy thereacross when employed in an severing mode but energy transfer by capacitive coupling when employed in a coagulating mode.

23 Claims, 5 Drawing Sheets

ELECTRIC FIELD CONCENTRATED ELECTROSURGICAL ELECTRODE

CROSS REFERENCES TO RELATED APPLICATIONS

This is a Continuation-in-Part of U.S. patent application Ser. No. 08/943,551 filed Oct. 3, 1997. The entirety of the disclosure thereof being specifically incorporated herein by reference.

BACKGROUND OF THE INVENTION

This invention relates to electrosurgery and more particularly to electrosurgical electrodes (e.g., probes, blades, forceps and the like) for use in performing electrosurgery. As is known to those skilled in the art, modern surgical techniques typically employ radio frequency (RF) cautery to cut tissue and coagulate the same to stop bleeding encountered in performing surgical procedures. For historical perspective and details of such techniques, reference is made to U.S. Pat. No. 4,936,842.

As is known to those skilled in the medical arts, electrosurgery is widely used and offers many advantages including that of the use of a single surgical tool for both cutting and coagulation. A variety of proposals have heretofore been embodied in existing electrosurgical implements. Examples of such proposals include those set forth in U.S. Pat. No. 4,534,347 granted to Leonard S. Taylor Aug. 13, 1985, U.S. Pat. No. 4,674,498 granted to Peter Stasz Jun. 23, 1987, and U.S. Pat. No. 4,785,807 granted to G. Marsden Blanch on Nov. 22, 1988.

The Taylor patent discloses an implement having a sharpened exposed edge (e.g., knife-blade like geometry) which is employed to perform conventional mechanical cutting of tissue while the blade is configured to act as a microwave radiator to transfer microwave energy by radiation into adjacent tissue to effect desired cauterization.

The Stasz patent sets forth several embodiments which disclose partly coated, partly exposed blades adapted for three modes of operation. These three modes are said to be: (1) a standard surgical cutting blade with a sharp edge when no electrical power is applied to it; (2) an electrocautery blade when a high voltage is applied between conductive surfaces of the blades sufficient to create a discharge arc therebetween for cutting and cauterizing of tissue; and (3) a low voltage cautery tool where $I^2R$ losses create heat to cauterize tissue.

The Blanch patent discloses an unsharpened blade which has been entirely coated with an insulating layer so that cutting is performed by electrical energy capacitively transferred through the insulating layer to the tissue which is to be cut rather than by conventional mechanical action. In such electrosurgery, "cutting" is accomplished when energy transfer is sufficient to cause water in tissue cells to boil, thus rupturing the cell membranes by internal rather than external forces. Relatively high energy levels have been required to effect such electrosurgical cutting While the Blanch proposals have constituted an important advance in the art and have found wide-spread acceptance in the field of electrosurgery, there has been a continuing need for further improvement in electrosurgery to effect in a relatively simple geometric configuration, a reduction in thermal necrosis thereby decreasing post-operative complication, reducing eschar production, reducing incidence of heat damage to tissue away from the cutting site, and increasing the speed of cutting.

BRIEF SUMMARY OF THE INVENTION

In a first embodiment, electrosurgical implements of the present invention are characterized by geometrical configurations that include non-stick insulation on the outer surface of most of the electrosurgical implement while exposing an uncoated minute sharpened cutting or probing surface at which electrosurgical energy is concentrated for enhanced cutting (and, in certain cases, coagulating) characteristics. For probes and blades, the electrosurgical implement is specially adapted for use in either a cutting or coagulation mode. In the cutting mode, the implement is positioned in a conventional cutting position in which the exposed blade or point is in contact with tissue that is to be cut. The presence of insulation over the blade other than at the point of cutting, together with the sharpened character of the exposed blade, concentrates the electrical energy at the point or line of contact; and while there may be some incidental capacitive coupling to adjacent tissue, it is insufficient to produce noticeable effects. When it is desired to provide coagulation, the relatively minute exposed cutting/probing surface is removed from tissue contact and one of the coated surfaces is disposed in contact with the tissue which is to be coagulated, thus switching the mode of energy transfer from that of essentially ohmic conduction (in the cutting mode) to capacitive coupling energy transfer in the coagulation mode. and thus facilitating both cutting and coagulation at reduced power levels. It has been found that such implement presents a marked improvement in performance over the proposals heretofore made by further concentrating electrosurgical energy, thus permitting more rapid and effective cutting at lower RF energy levels while resulting in reduced thermal necrosis, more rapid cutting, and reduced eschar production. The principles hereof may not only be applicable to blades, points and forceps, but also to modified ball electrodes, L-hooks, L-wires, J-hooks and similar constructions.

For another embodiment of the invention such as bi-polar forceps, it has been found that the principles of energy concentration may be advantageously employed to facilitate coagulation. There, since the forceps are not normally used for cutting, the energy concentration is embodied in a number of parallel edges that may be either partly exposed or entirely coated with non-stick coating depending upon the particular circumstances of use.

OBJECTS AND FEATURES OF THE INVENTION

It is one general object of the invention to improve electrosurgical implements.

It is another object of the invention to focus and/or concentrate electrosurgical energy in electrosurgical implements.

It is yet another object of the invention to improve accomplishment of surgical procedures through electrical cutting of tissue.

It is still another object of the invention to simplify electrosurgical implements in a configuration that requires reduced power levels while reducing undesired tissue trauma and production of eschar.

Accordingly, in accordance with one feature of the invention, an electrosurgical implement is structured geometrically to include one or more relatively small exposed working regions at which electric transfer is concentrated, thus facilitating surgical procedures.

In accordance with yet another feature of the invention, the aforementioned concentration of electric energy transfer results in a corresponding increase in focused transfer of electrical energy to defined locations and thus lessens undesired transfer to adjacent tissue.

In accordance with still another feature of the invention, the aforementioned concentration of energy permits use of reduced levels of electrosurgical power thus improving performance and safety.

In accordance with one further feature of the invention, most of the electrosurgical implement is coated with a high dielectric strength non-stick coating thus facilitating removal of the small exposed surface from contact with tissue and the positioning of a coated surface in contact with material for which cauterization is to be effected whereby electrical energy may be transferred by capacitive coupling through the coating to the material for cauterizing such material.

These and other objects and features of the invention will be apparent from the following description, by way of example of preferred embodiments, with reference to the drawing.

DESCRIPTION OF A PREFERRED EMBODIMENT

As employed in this specification and the appended claims, the following terms shall have the meanings as now defined.

"Operative Surface" means an exposed surface of the energy-conducting member extending outwardly from beneath covering insulation by a distance of 0.2 mm or less.

"Non-stick Material" means any of a group of conventional and well-known materials use d in this art as coatings to eliminate or reduce adherence of tissue, blood and the like to electrosurgical blades. Examples are coatings of diamond material or fluorinated hydrocarbons (PTFE), an example of the latter being that which is commercially available under the trade name TEFLON.

Figure 1:
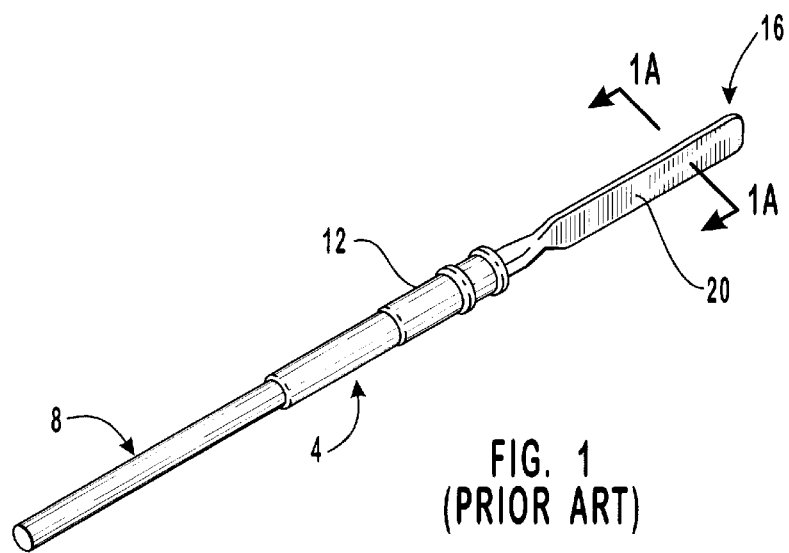
FIG. 1 is a perspective view illustrating an implement representative of the prior art.
Figure 1A:
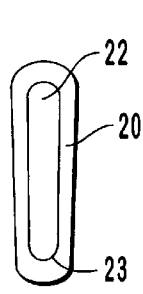
FIG. 1A is a sectional view taken along section lines 1A—1A of FIG. 1.

Now turning to the drawing, and more particularly FIGS. 1 and 1A thereof, they will be seen to depict an implement representative of the prior art as set forth in the aforementioned Blanch U.S. Pat. No. 4,785,807. There, are seen an electrosurgical knife, generally shown at 4, having a proximal end 8 fitted with a sleeve fitting 12 positioned around the knife shank to provide protection and to facilitate holding of the knife by a conventional holder (not shown). The knife also includes a distal end 16 formed with unsharpened cutting surface 23 as shown. A coating 20 of non-stick material covers the surface area 22 of the cutting blade and serves to eliminate or reduce the clinging of charred tissue to the blade.

Figure 2B:
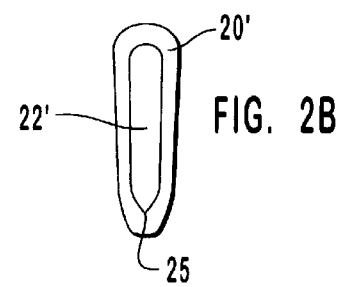
FIG. 2B is a drawing similar to that of FIG. 2A except for the working surface of the implement which is depicted as a knife edge.
Figure 2A:
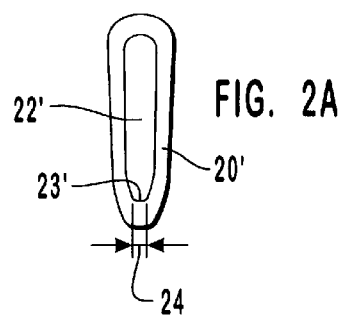
FIG. 2A is a sectional view taken along the section lines 2A—2A of FIG. 2 and depicting a partly sharpened working surface.
Figure 2:
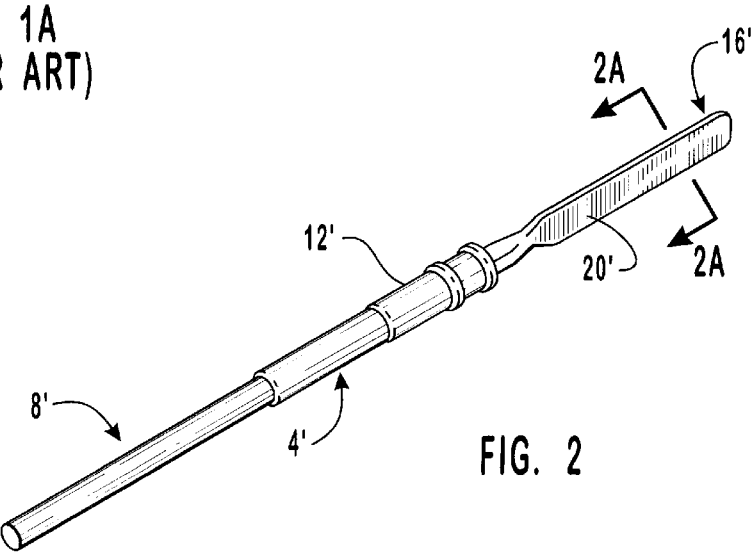
FIG. 2 is a similar perspective view of an implement embodying principles according to the invention.
Figure 4:
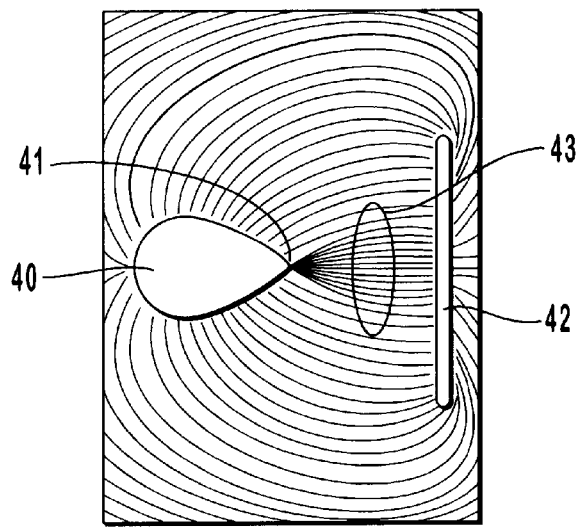
FIG. 4 is a view illustrating modified electric field concentration associated with a sharply pointed geometry.

FIG. 2 depicts an implement which embodies the principles underlying the instant invention. There, in FIG. 2 is seen an instrument appearing similar to that of FIG. 1. Thus, in FIG. 2 there is seen an electrosurgical knife, generally shown at 4', having a proximal end 8' fitted with a sleeve fitting 12' positioned around the knife shank to provide protection and to facilitate holding of the knife by a conventional electrosurgical holder (not shown). The knife also includes a distal end 16' which is formed with a special geometrical shape as described in connection with FIGS. 2A, 4 and 5. A coating 20 of non-stick material covers the surface area of the cutting blade and serves to eliminate or reduce the clinging of charred tissue to the blade. In sharp contrast with the embodiment of FIG. 1, however, the embodiment illustrated in FIG. 2 features a cross sectional geometry which includes an edge that is at least partly sharpened as shown in FIG. 2A.

As mentioned above, FIG. 2A is a sectional view taken along the section lines 2A—2A of FIG. 2. There, it will be seen are electrically conductive main body 22 which may be of any suitable material such as, preferably, surgical grade stainless steel. Body 22 has been at least partly sharpened at its lower extremity to a knife edge or point 23' which, as described in connection with FIGS. 3 and 4 concentrates or focuses the electric field created when electrical potential is applied to the blade, thus increasing the concentration of transferred electrical energy and correspondingly improving efficiency with which the implement achieves a cutting action, e.g., severs tissue. Before leaving FIG. 2A, it should be understood that while the preferred geometry embodies a fully sharpened edge (or point) such as that depicted in FIG. 2B, the efficacious characteristics flowing from the invention begin to be significantly observed when the dimension 24 (i.e., working edge width) is at or less than 0.2 mm, thus presenting a working edge width of 0.2 mm or less; and such efficacious characteristics further improve as the dimension 24 is reduced to a knife edge.

Figure 3:
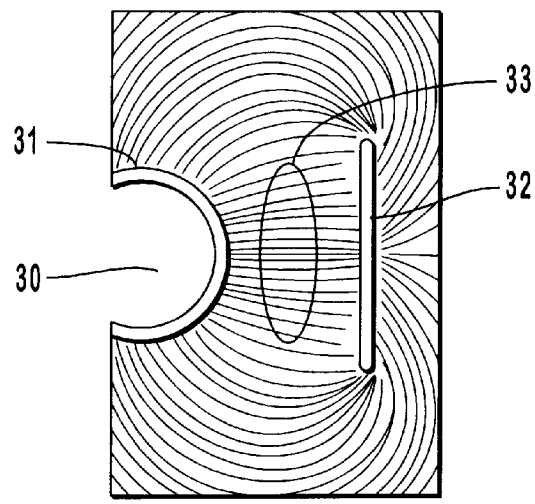
FIG. 3 is a view illustrating a typical electric field existing between a rounded surface implement and a working return electrode.

Now turning to FIG. 2B, there will be seen a configuration similar to that of FIG. 2A except that in FIG. 2B there is depicted a fully sharpened blade having a knife edge 25. The physical principles underlying the foregoing marked improvement can be understood from reference to FIGS. 3 and 4. FIG. 3 is a diagram illustrating electric field pattern lines for an electric field existing between a conductor or electrode 30 having an annular, or curved, exterior surface 31 and a counter electrode 32. Although electrode 30 is shown as being hollow, the electric field pattern shown will be essentially the same if the electrode were solid. It will now be seen that the density of the electric field lines within ellipse 33 is nearly uniform and thus tile electric field does not vary substantially within that region. However, in FIG. 4, it will be noted that if the geometry of electrode 40 is made to include a pointed region as represented by point or edge 41, the corresponding electric field becomes much more concentrated as represented by the much greater line density of electric field lines (within the ellipse 43) between the electrode 40 and counter electrode 42. Thus, on an irregularly shaped conductor, charge tends to accumulate at locations where the curvature of the surface is greatest, that is, at sharp points or edges. By sharpening the blade edge in accordance with the invention hereof, the charge is concentrated along a much smaller surface area or region thus focusing the electric field lines into a tighter arrangement which reduces extraneous charge loss in tissue which is not in close proximity to the point or sharpened edge. The cutting edge of the electrode need not be sharply pointed, it need only be shaped (sharpened) to concentrate energy transfer to the degree desired for optimum cutting.

By way of illustration, the conventional electrode of FIG. 1 has an edge 23 thickness of about 0.33 mm and in the cutting mode may utilize a power setting nearing 40 watts. When sharpened to an edge 23' thickness of about 0.00735 mm, a "sharpness" below that required of a mechanical scalpel blade, the electrode of FIG. 2 can quickly cut through tissue at less than 20 watts, a power setting of 50% less than that required for the electrode of FIG. 1. Moreover, such blade of FIG. 2 cuts more rapidly with less resistance, less eschar production, less thermal necrosis, and improved operator control.

Figure 5:
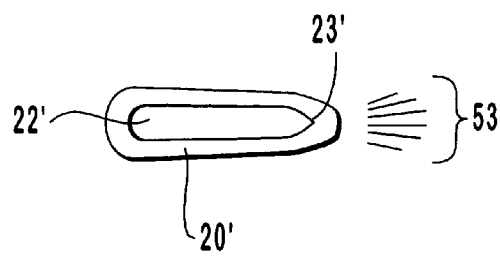
FIG. 5 is a simplified view illustrating a typical concentration of electric field projected from the partly sharpened edge of FIG. 2A.

The foregoing principles are illustrated in FIG. 5. As noted above, FIG. 5 is a simplified view illustrating a typical concentration of electric field projected from the sharpened edge of FIG. 2A. To facilitate clarity and simplicity of presentation, only lines 53 representing the electric field in the direction of the sharpened point or edge 23 are shown.

It will be observed that the electrode of FIG. 5 is that earlier illustrated in FIG. 2A. Thus, there are shown electrically conductive main body 22 with at least partly sharpened edge or point 23' completely coated with insulating coating 20'. When electrosurgical potential is applied to body 22 in the presence of tissue for which severance is desired, the density of energy transfer is concentrated at the apex 23' as represented by the longer rays within bundle of rays 53. Thus, in the illustrated example, energy is concentrated along the principal axis of the main body extended from edge 23'.

The insulating coating 20' may be any of the known several non-stick materials (as defined above) that have been found attractive for use in electrosurgery and applied by any of the known techniques. However, in accordance with the preferred embodiment hereof, such material is a fluorinated hydrocarbon (PTFE), an example of which is that which is commercially available under the trade name Teflon.

The thickness of the non-stick material of the embodiments of FIGS. 2A and 2B is that sufficient to ensure transmission of radio frequency electrical energy from the coated main body to the tissue of the patient essentially exclusively by capacitive coupling, ordinarily less than 1 mil. The precise optimum thickness will vary depending upon the material used and can be readily determined by routine experimentation. It will be evident that this coating mechanically "dulls" any sharp electrode edge, but as previously noted, cutting by electrosurgery does not necessarily require sharp surgical edges for mechanically severing tissue. Rather, the cutting is effected by utilizing sufficient energy to cause water in the tissue cells to boil and rupture the cell membranes.

Figure 6:
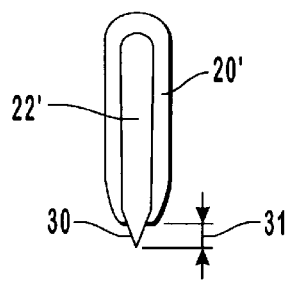
FIG. 6 is a view illustrating an alternative embodiment of the invention in which a minute region of a sharpened blade projects a predetermined distance outwardly from beneath a mostly-coated blade to expose the edge.

The energy concentration principles according to the invention may additionally be efficacious when employed with an implement such as the embodiment of FIG. 6. There, as will be observed from reference to the Figure, an exposed Operative Surface 30 as defined above is shown of electrically conducting main body 22 extending outwardly from beneath covering insulation by a distance 31 of 0.2 mm or less. It has been found that 0.2 mm marks the approximate limit of extension in typical surgical blades in order to achieve optimum energy concentration while preserving the insulation character of the remainder of the blade to facilitate coagulation. When in use, the energy concentrated at the exposed sharpened blade is particularly efficacious in achieving tissue severance. When it is desired to employ the blade in a coagulation mode, the exposed surface is withdrawn from contact with tissue and the insulated side of the blade is disposed in contact with the area at which coagulation is desired. Thus, in the embodiment of FIG. 6, tissue severance is achieved principally by ohmic conduction through concentration of energy at the sharpened surface, while coagulation is achieved principally through capacitive transfer of energy across the insulation 20'.

Figure 7:
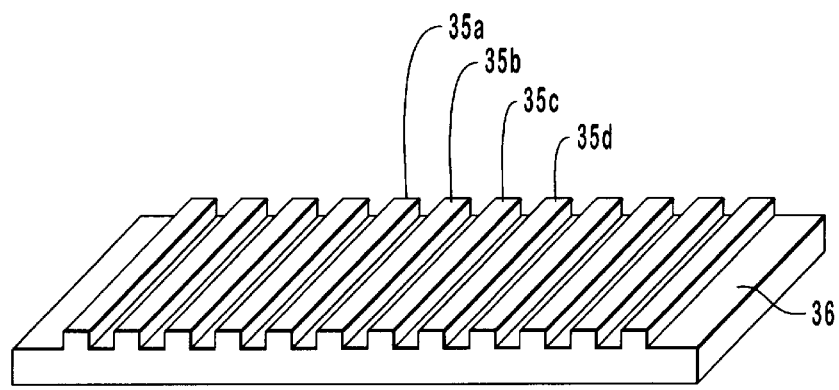
FIG. 7 is a view of a portion of the grasping surface of an electrosurgical forceps according to the prior art.
Figure 8:
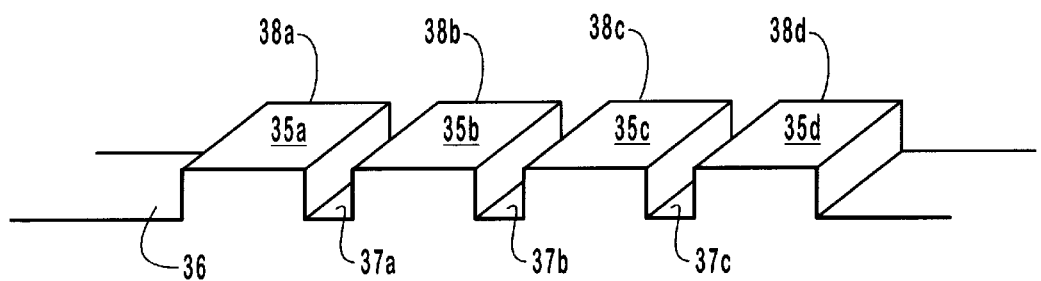
FIG. 8 is a schematically depicted enlarged view of the grasping surface of the prior art forceps of FIG. 7.

As mentioned above, the energy concentration principles according to the invention are applicable to other medical instruments such as forceps. FIGS. 7 and 8 illustrate typical bi-polar electrical forceps surfaces according to the prior art. There, in FIG. 7 is a view of a portion of the grasping surface of typical electrosurgical forceps according to the prior art. As will be observed, there are squared top ridges 35a, b, c and d (illustrated in enlarged form in FIG. 8) projecting upwardly from principal surface 36. The square tops of these ridges are separated by generally rectangular valleys 37a, 37b and 37c. Thus, there are relatively broad area working surfaces 38a, 38b, 38c and 38d which result in correspondingly large surface contact areas with tissue when the forceps are in use.

As mentioned above, FIGS. 9 and 10 are views generally similar to those of FIGS. 7 and 8 but depicting a portion of the grasping surface of electrosurgical forceps according to the invention. There, it will be seen are upwardly pointing projections 40a, 40b, 40c and 40d that are sharpened to edges 41a, 41b, 41c and 41d and which are operative to concentrate energy according to the principles described above in connection with FIGS. 2A, 2B and 6. Thus, such knife edges may be: slightly dulled and entirely coated with insulation as exemplified by FIG. 2A; highly sharpened and entirely coated with insulation as exemplified by FIG. 2B, or partly uncoated to present exposed operative surfaces as exemplified by FIG. 6. In any event, the highly concentrated areas provided for engagement with patient tissue result in a high concentration of electrical energy when the forceps are operated in their coagulating mode, thus markedly improving their characteristics.

Figure 9:
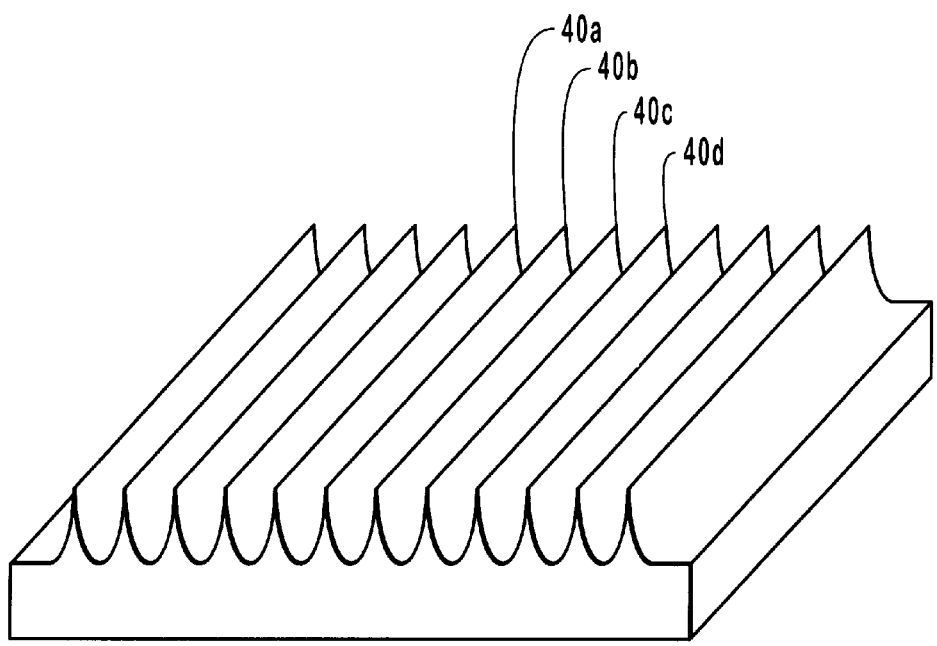
FIG. 9 is a view generally similar to that of FIG. 7 but depicting a portion of the grasping surface of an electrosurgical forceps according to the invention.
Figure 10:
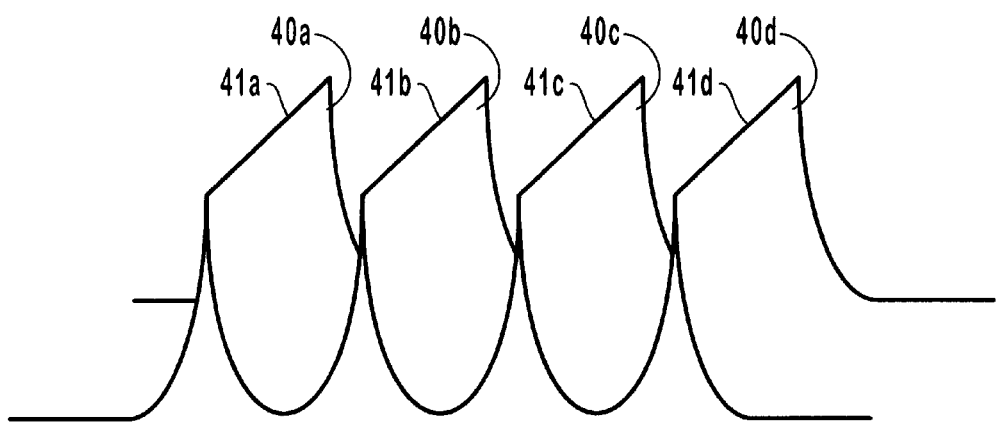
FIG. 10 is a schematically depicted enlarged view of the grasping surface of the forceps of FIG. 9.
Figure 11:
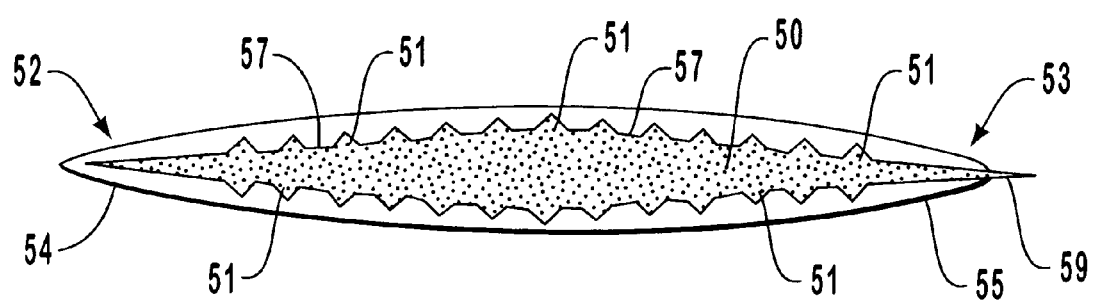
FIG. 11 is a cross section illustrating a further variation on the structure of FIGS. 6, 9 and 10 in which one extremity of a blade is coated, the opposite extremity includes an exposed Operative Surface as defined herein, and in which the sides of the blade include a series of abrupt geometrical anomalies to provide relatively sharp surface changes thereby to enhance energy concentration.

As mentioned above, FIG. 11 is a cross section illustrating a further variation on the structure of FIGS. 6, 9 and 10 in which one extremity of a blade is coated, the opposite extremity includes an exposed Operative Surface as defined herein, and in which the sides of the blade include a series of abrupt geometrical anomalies to provide relatively abrupt surface changes thereby to enhance energy concentration. There, in FIG. 11 is a main conductive body 50 having upper and lower surfaces containing miniature peaks 51 distributed substantially uniformly therealong so as to embody the energy concentrating characteristics hereinabove described. While end 52 is completely covered with insulation 57, end 53 has been modified to expose an operative surface 59. Accordingly, there has been included in a single electrosurgical implement a combination of the features described hereinabove: namely, a covered severing part (the left end of FIG. 11); upper and lower lateral coagulating surfaces including energy concentrating peaks 51; and an exposed operative surface 59 at the right side of the implement.

It will now be evident that there has been described herein an improved electrosurgical implement which provides a marked improvement in performance.

Although the invention hereof has been described by way of preferred embodiments, it will be evident that adaptations and modifications may be employed without departing from the spirit and scope thereof.

The terms and expressions employed herein have been used as terms of description and not of limitation; and thus, there is no intent of excluding equivalents, but on the contrary it is in tended to cover any and all equivalents that may be employed without departing from the spirit and scope of the invention.

What is claimed is:

1. An electrosurgical electrode member for performing operative procedures on a patient comprising a conducting electrode having a main body formed with a plurality of peaked portions that extend therefrom, said main body being adapted for communicating radio frequency electrical energy to patient tissue for performing operative procedures thereupon, an insulating coating covering said main body except for an operative surface angularly orientated with respect to said plurality of peaked portions, energy concentrating means including said operative surface for concentrating electrical energy transferred from said operative surface to tissue of said patient when said operative surface engages said tissue, and means including said insulating coating effective when said operative surface is not in contact with said tissue and when said insulating coating is in contact with said tissue for transferring electrical energy across said coating by capacitive coupling to said tissue for cauterizing said tissue.

2. A member according to claim 1 wherein said operative surface is a point.

3. A member according to claim 1 wherein said electrosurgical electrode member is one part of a pair of bipolar electrosurgical forceps.

4. A member according to claim 3 wherein said one part further includes a plurality of discrete spaced operative surfaces.

5. A member according to claim 4 wherein said plurality of discrete spaced operative surfaces are substantially parallel to each other.

6. A member according to claim 1 wherein said operative surface is a knife edge.

7. A member according to claim 6 wherein said knife edge is at least partly sharpened.

8. A member according to claim 7 wherein said partly sharpened edge presents a working edge width of 0.2 millimeters or less.

9. A member according to claim 6 wherein said knife edge is fully sharpened.

10. A member according to claim 1 wherein said insulating coating is non-stick material.

11. A member according to claim 1 wherein said insulating coating is a capacitor dielectric.

12. A member according to claim 11 wherein said insulating coating is of non-stick material.

13. A member according to claim 1 wherein said insulating coating comprises a fluorinated hydrocarbon material or diamond.

14. A member according to claim 13 wherein said insulating coating consists essentially of diamond.

15. A member according to claim 13 wherein said insulating coating consists essentially of fluorinated hydrocarbon.

16. A member according to claim 1 wherein said plurality of peaked portions includes a first edge of a first peaked portion being disposed at a first extremity of said electrode, and a second edge of a second peaked portion being disposed at a second extremity of said electrode opposite said first extremity.

17. A member accord ing to claim 16 wherein said conducting electrode further includes a second pair of edges having a first additional edge and a second additional edge, said additional edges of said second pair being disposed substantially at right angles to said first edge and said second edge of said plurality of peaked portions, and wherein said first additional edge is completely covered by said insulating coating, and wherein said second additional edge includes an exposed operative surface.

18. A method of using an electrosurgical implement having a main body formed with a plurality of peaked portions that extend therefrom, the main body being adapted for communicating radio frequency electrical energy to patient tissue for performing operative procedures thereupon, the electrosurgical implement further including an insulating coating covering the main body except for an operative surface angularly orientated with respect to the plurality of peaked portions and energy concentrating means including the operative surface for concentrating electrical energy transferred from the operative surface to tissue of said patient when the operative surface engages the tissue, wherein the method comprising the steps of:

a. contacting said operative surface with patient tissue while energizing said implement with radio-frequency electrical energy thereby to sever said tissue;

b. removing said operative surface from contact with said patient tissue;

c. identifying a patient site needing coagulation;

d. contacting at least a part of said insulating coating covering said electrosurgical implement with said patient site needing coagulation; and e. energizing said implement with radio-frequency electrical energy while contacting said coating with said patient site thereby to provide coagulation to said site.

19. An electrosurgical electrode member for performing operative procedures on a patient comprising a conducting electrode having a main body adapted for communicating radio frequency electrical energy to patient tissue for performing operative procedures thereupon, said main body being formed with a first surface and a second surface and having a plurality of peaked portions extending from at least one of said first surface and said second surface, an insulating coating covering said main body except for an operative surface, energy concentrating means including said operative surface for concentrating electrical energy transferred from said operative surface to tissue of said patient when said operative surface engages said tissue, and means including said insulating coating effective when said operative surface is not in contact with said tissue and when said insulating coating is in contact with said tissue for transferring electrical energy across said coating by capacitive coupling to said tissue for cauterizing said tissue.

20. A member according to claim 19 wherein said plurality of peaked portions are uniformly distributed over at least one of said first surface and said second surface.

21. A member according to claim 19 wherein at least one side of each peaked portion of said plurality of peaked portions is generally planar.

22. A member according to claim 20 wherein each said peaked portion of said plurality of peaked portions is formed with at least one edge.

23. A member according to claim 22 wherein at least one of said plurality of peaked portions is formed on said first surface and said second surface such that said at least one edge of said peaked portion on said first surface is opposite to said at least one edge of said peaked portion on said second surface.

* * * * *

UNITED STATES PATENT AND TRADEMARK OFFICE
CERTIFICATE OF CORRECTION

PATENT NO. : 6,066,137
DATED : May 23, 2000
INVENTOR(S) : Darcy W. Greep

It is certified that error appears in the above-identified patent and that said Letters Patent are hereby corrected as shown below:

Col. 4, ln. 5: after "material" change "use d" to --used--

Col. 5, ln. 7: after "thus" change "tile" to --the--

Col. 5, ln. 61: after "name" change "Teflon" to --TEFLON--

Col. 7, ln. 24: after "it is" change "in tended" to --intended--

Col. 8, ln. 25: after "member" change "accord ing" to --according--

Signed and Sealed this

Twenty-second Day of May, 2001

*Attest:*

NICHOLAS P. GODICI

*Attesting Officer*     Acting Director of the United States Patent and Trademark Office